United States Patent [19]

Childress et al.

[11] 4,301,036
[45] Nov. 17, 1981

[54] DEHYDRATION CATALYST FOR MAKING ETHYLENIMINE

[75] Inventors: David L. Childress, Angleton; William V. Hayes, Clute, both of Tex.

[73] Assignee: The Dow Chemical Company, Midland, Mich.

[21] Appl. No.: 170,318

[22] Filed: Jul. 18, 1980

[51] Int. Cl.³ .................. B01J 23/30; B01J 21/08
[52] U.S. Cl. ................................ 252/458; 252/443
[58] Field of Search ........................ 252/443, 458

[56] References Cited

U.S. PATENT DOCUMENTS

| | | | |
|---|---|---|---|
| 2,382,581 | 8/1945 | Ruthruff | 252/458 X |
| 2,441,966 | 5/1948 | Hale | 252/443 X |
| 2,755,228 | 7/1956 | Anhorn et al. | 252/443 X |
| 3,518,206 | 6/1970 | Sowards et al. | 252/458 X |

*Primary Examiner*—Carl F. Dees
*Attorney, Agent, or Firm*—A. C. Ancona

[57] ABSTRACT

A dehydration catalyst containing tungsten oxide on a low surface area support and having a silica coating thereon. The catalyst has increased life and is useful for the dehydration of alkanolamines in making alkylenimines, e.g. ethanolamine is dehydrated to ethylenimine.

5 Claims, No Drawings

DEHYDRATION CATALYST FOR MAKING ETHYLENIMINE

BACKGROUND OF THE INVENTION

Ethylenimine (EI) is an active three-membered cyclic amine and is a very useful compound since it can introduce an amino group by an addition reaction, substitution reaction, ring opening reaction and the like. Ethylenimine is especially important as an aminoethylation agent of compounds containing an active hydrogen. It is also useful as a monomer for polyamine-type polymers in homo and co-polymerizations. In addition to all of these uses, it is also possible to prepare derivatives which retain the ring opening reactivity of ethylenimine through an addition reaction of the amino group. All of these features make ethylenimine an important substance both chemically and industrially.

Ethylenimine can be synthesized by one of several methods. One is the Gabriel method in which a beta-halo-ethylamine undergoes a ring closure through a treatment with a concentrated base or silver oxide. Another involves the reaction of ethylene chloride (1,2-dichloroethane) with anhydrous ammonia in the presence of a base. This reaction and equivalent reactants for form EI and substituted EI's are disclosed in U.S. Pat. No. 3,336,294. Yet another preparation of EI involves a decomposition (ring closure) of monoethanolamine sulfuric acid ester by hot concentrated base. Each of the above methods present certain disadvantages. For example, it is necessary to control the reaction conditions strictly to synthesize both beta-haloethyl amine and monomethanolamine sulfuric acid ester. The syntheses tend to be accompanied by side reaction and side products. All of these problems make these starting materials very expensive. At the same time, the halogen and sulfuric acid ester group which are introduced in the syntheses are removed in the subsequent process making these syntheses wasteful from the stand point of the functional group utilization. Furthermore, both processes use a base for the ring closure reaction. The bases most often used are sodium hydroxide and potassium hydroxide and these bases are used as concentrated solutions in large quantities. Thus the base requirement per ethylenimine unit is very high and uneconomical. The by-products, NaCl, $Na_2SO_4$ or the potassium equivalents, are a further expense since they have little value and must be disposed of. The lost chlorine values in the method using 1,2 dichloroethane makes this process an expensive one. None of the art processes are readily made continuous so as to be more attractive commercially.

A more recent process involving the vapor phase dehydration of monoethanolamine is disclosed in Japanese Patent Publication No. 50-10593/1975. A catalyst of tungsten oxide alone or preferable with another metal oxide as an assistant is employed. The metal oxide assistant includes lithium, magnesium, tin, bismuth, molybdenum, nickel and aluminum oxides.

Such assistants or promoters may be added to the catalyst in known manner by depositing a promoter metal or oxide on the catalyst support either prior to, coincidentally with or after the deposition of the catalytic material. The reaction is conducted at a temperature of 350° C. to 450° C. preferably using an inert diluent gas such as ammonia or nitrogen. Conversions of up to 45% and selectivities of as high as 66% are reported.

It has now been discovered that a coating of silica over a tungsten oxide catalyst improves its life and maintains the selectivity and conversion close to the 50% level. Without the silica addition both selectivity and conversion fall off rapidly.

SUMMARY OF THE INVENTION

An inert support, e.g. silicon carbide, is coated with tungsten oxide by soaking the support in a solution containing a soluble salt of tungsten, e.g. ammonium metatungstate, after which it is dried and calcined. Thereafter it is soaked in a colloidal solution of $SiO_2$ dried and calcined to provide a coating of silica on the surface of the catalyst.

Tungsten catalysts prepared according to the art have the tendency to diminish in activity and selectivity over a relatively short period of time. The present invention is the discovery that a coating of silica on the surface of such a catalyst effectively prevents the diminution of activity.

DETAILED DESCRIPTION OF THE INVENTION

The present invention is an improved catalyst which is useful for the dehydration of alkanolamine to make alkylenimines. The catalyst is prepared by a known method, i.e. soaking a support in an aqueous solution of the soluble metal salt of tungsten. After removing excess solution and drying the tungsten oxide is formed by calcining the impregnated support in air at a temperature in the range of 500° to 900° C. for a period of time of from 1 to 4 hours. In like manner the tungsten oxide catalyst which has been soaked in the silica solution is again calcined in air for 1–3 hours at 350°–500° C.

The catalyst supports suitable for the present invention are inert low surface area materials such as silicon carbide, spinel, alumina, and magnesium-alumina silicate. The surface area of such supports should be from about 0.02 to about 1 $m^2/g$.

The amount of tungsten oxide deposited on the support should be in the range of from 5 to 50% and preferably from about 27 to 43% based on the support and catalyst. The promoter, i.e. silicon dioxide, is preferably applied at a concentration of from 1 to about 10% based on total weight of catalyst.

In the process of dehydration, the molar ratios of the feed components may vary from 12.6 to 33.1 ammonia and 7.4 to 32.8 nitrogen per mole of alkanolamine.

The following examples show the preparation and use of the catalysts of the art and of the present invention.

EXAMPLE 1

(Comparative)

A tungsten catalyst was prepared in the manner of the prior art in the following manner: Ammonium metatungstate (137.9 gms) was dissolved in 250 mls of deionized water. This solution was then added to 280 gms of low surface area 3/16 inch spherical silicon carbide support. The excess water was removed on a steam bath and the supported catalyst oven dried at 150° C. for one hour. The catalyst was then air-calcined in a furnace for four hours at 710° C. using an air flow of 15 SCF/hr. Loading of tungsten oxide on the support was 29.8 wt. %.

EXAMPLE 2

About 75 ml of this catalyst was loaded into a ¾ inch I.D. stainless steel single tube reactor and run under the following conditions: reactor temperature—400° C.; ammonia—3626 mls/min.; nitrogen—300 mls/min.; liquid monoethanolamine—0.35 mls/min.; liquid water—0.8 mls/min.

minutes. The excess was drained off and the catalyst oven dried at 150° C. for one hour and calcined in an air furnace as described above. A 2.68 wt. % loading of silicon dioxide was burdened on the catalyst. Surface area was 2.47 $m^2/gm$.

Into a ¾ inch I.D. stainless steel single tube reactor 75 mls of each of the catalysts was loaded and run under the conditions shown in the Table below.

| | Catalyst | | Temp. | Feed Composition (ml/min) | | | | | |
|---|---|---|---|---|---|---|---|---|---|
| Example | % $WO_3$ | % $SiO_2$ | (°C.) | $NH_3$ | $N_2$ | MEA* | Water* | Conv. % | Sel. % |
| 3 (Comp) | 33.2 | — | 410 | 3625 | 350 | 0.4 | 0.8 | 24.2 | 13.0 |
| 4** | 33.2 | 2.68 | 410 | 3625 | 350 | 0.4 | 0.8 | 17.9 | 41.5 |
| 5 | 11.3 | 3.64 | 410 | 909 | 2980 | 0.4 | 0.8 | 35.6 | 56.0 |
| 6 | 30.7 | 1.94 | 410 | 909 | 2980 | 0.4 | 0.8 | 25.0 | 50.9 |
| 7 | 22.8 | 2.87 | 400 | 909 | 2980 | 0.4 | 0.8 | 63.7 | 58.9 |
| 8 | 30.7 | 1.17 | 410 | 3625 | 350 | 0.4 | 0.8 | 28.5 | 53.3 |

*MEA, water amounts are expressed as liquid rather than vapor as with $NH_3$ and $N_2$.
**Catalyst of Example 3 ran all day without a die off, but was then subjected to a regeneration treatment as in Example 2 with air and steam for one hour at 410° C. and run the next day at 17.8% MEA conversion. The EI selectivity increased to 52.2%. Catalyst was run for five days with selectivity increasing with each regeneration.

With a 31.4% MEA conversion, the selectivity to EI dropped from 41% to 14% over a two-hour period. After regeneration with air and steam at 400° C. for 1½ hours, MEA conversion was 23% with EI selectivity at a high of 12.2% down to 4% after 2 hours.

EXAMPLE 3

(Comparative)

To prepare the catalyst of the present invention 124.1 gms of ammonium metatungstate was dissolved in 250 mls of deionized water. This solution was then added to 230 gms of low surface area 3/16 inch spherical silicon carbide support. The excess water was removed on a steam bath and the supported catalyst oven dried at 150° C. for one hour. The catalyst was then calcined in an air furnace for four hours at 715° C. and 15 SCF hr air. Loading of tungsten oxide on the support was 33.2 wt. %. Surface area of support (finished catalyst) was 0.13 $m^2/gm$.

EXAMPLE 4

(Invention)

Half of the above catalyst (Example 3) was soaked in a 10% solution of colloidal silicon dioxide for a few The regeneration can be conducted at 300° to 500° C. for 1 to 3 hours.

We claim:

1. The process of preparing a tungsten catalyst suitable for dehydrating an alkanolamine in the vapor phase to produce an alkylenimine by applying a soluble salt of tungsten from a solution thereof to a low surface area support, calcining said salt to tungsten oxide and thereafter applying silica to the catalyst as a promoter thereby improving the life of said tungsten catalyst.

2. The process of claim 1 wherein the catalyst produced contains from about 5 to about 50% $WO_3$ and from about 1 to about 10% $SiO_2$.

3. The process of claim 1 wherein the catalyst produced contains from about 11 to about 34% $WO_3$ and 1 to 4% $SiO_2$.

4. The process of claim 1 wherein the calcining is accomplished by heating in air at a temperature of 500° to 900° C.

5. The process of claim 3 wherein the silica is applied to the support from a solution and thereafter dried and calcined by heating in air at a temperature of 300° to 500° C.

* * * * *